United States Patent
Kuroiwa et al.

(10) Patent No.: US 10,390,794 B2
(45) Date of Patent: Aug. 27, 2019

(54) ULTRASOUND DIAGNOSTIC APPARATUS AND ULTRASOUND PROBE

(71) Applicant: TOSHIBA MEDICAL SYSTEMS CORPORATION, Otawara-Shi (JP)

(72) Inventors: Koji Kuroiwa, Nasushiobara (JP); Tatsuo Ogasawara, Otawara (JP); Kazuhito Nakata, Otawara (JP); Gen Nagano, Nasushiobara (JP); Kenichi Unayama, Otawara (JP); Takeshi Fukasawa, Nasushiobara (JP); Fumio Mochizuki, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 1171 days.

(21) Appl. No.: 14/189,187

(22) Filed: Feb. 25, 2014

(65) Prior Publication Data

US 2014/0171802 A1   Jun. 19, 2014

Related U.S. Application Data

(63) Continuation of application No. PCT/JP2013/067246, filed on Jun. 24, 2013.

(30) Foreign Application Priority Data

Aug. 7, 2012   (JP) .................................. 2012-175203
Jun. 17, 2013   (JP) .................................. 2013-126815

(51) Int. Cl.
  *A61B 8/00*   (2006.01)

(52) U.S. Cl.
  CPC .......... *A61B 8/4477* (2013.01); *A61B 8/4411* (2013.01); *A61B 8/4438* (2013.01);
  (Continued)

(58) Field of Classification Search
  None
  See application file for complete search history.

(56) References Cited

U.S. PATENT DOCUMENTS

| 6,370,411 | B1 | 4/2002 | Osadchy et al. |
| 2003/0014645 | A1* | 1/2003 | Sambati ............... G06F 21/445 |
| | | | 713/182 |

(Continued)

FOREIGN PATENT DOCUMENTS

| JP | 7-391 A | 1/1995 |
| JP | 11-70109 A | 3/1999 |

(Continued)

OTHER PUBLICATIONS

English translation of JP 2010-069178 provided by the AIPN machine translation tool.*

(Continued)

*Primary Examiner* — Katherine L Fernandez
(74) *Attorney, Agent, or Firm* — Oblon, McClelland, Maier & Neustadt, L.L.P.

(57) ABSTRACT

An ultrasound diagnostic apparatus includes an ultrasound probe with transducers, memory storing probe identification information and binary state generation unit generating a binary electrical state corresponding to a probe identifier, probe identifier conversion unit converting the electrical state into the probe identifier, read unit reading the probe identification information from the memory, determination unit determining consistency between the probe identifier after conversion and the probe identification information read from the memory, and warning output unit outputting a predetermined warning if the probe identifier is inconsistent with the probe identification information.

4 Claims, 9 Drawing Sheets

(52) U.S. Cl.
CPC .............. *A61B 8/4483* (2013.01); *A61B 8/54* (2013.01); *A61B 8/56* (2013.01); *A61B 8/4444* (2013.01)

(56) References Cited

U.S. PATENT DOCUMENTS

| | | | |
|---|---|---|---|
| 2004/0171935 A1* | 9/2004 | Van Creveld | A61B 8/00 600/437 |
| 2004/0220463 A1* | 11/2004 | Satoh | A61B 8/00 600/407 |
| 2009/0069690 A1* | 3/2009 | Shin | A61B 8/00 600/459 |
| 2010/0305442 A1 | 12/2010 | Tierney et al. | |

FOREIGN PATENT DOCUMENTS

| | | |
|---|---|---|
| JP | 11-299781 A | 11/1999 |
| JP | 2001-520565 A | 10/2001 |
| JP | 2002-602 A | 1/2002 |
| JP | 2002-172116 A | 6/2002 |
| JP | 2010-69178 A | 4/2010 |

OTHER PUBLICATIONS

International Search Report dated Jul. 16, 2013 for PCT/JP2013/067246 filed on Jun. 24, 2013 with English Translation.
International Written Opinion dated Jul. 16, 2013 for PCT/JP2013/067246 filed on Jun. 24, 2013.
International Preliminary Report on Patentability and Written Opinion dated Feb. 19, 2015 in PCT/JP2013/067246.
Office Action dated Nov. 15, 2016 in Japanese Patent Application No. 2013-126815.

* cited by examiner

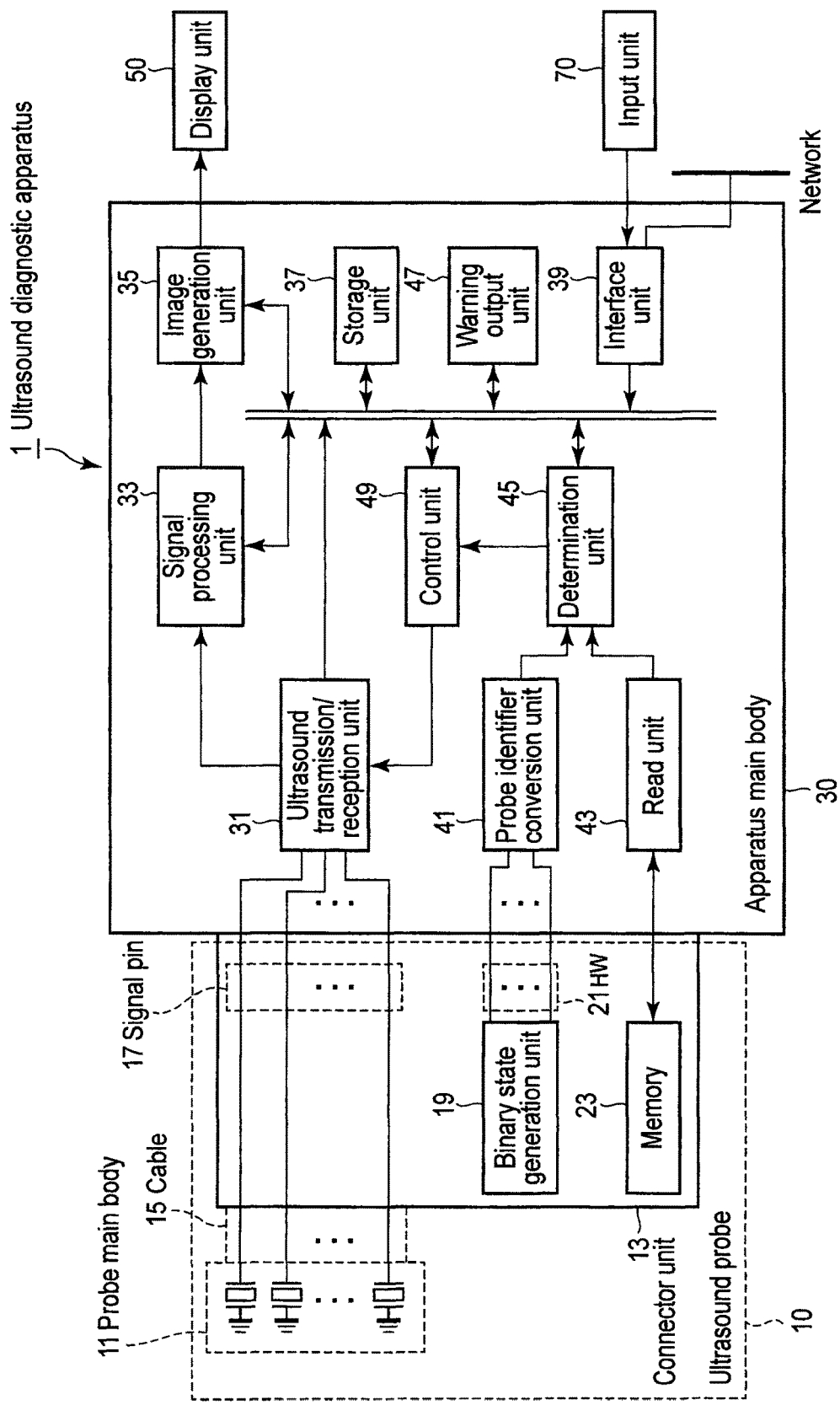
F I G. 1

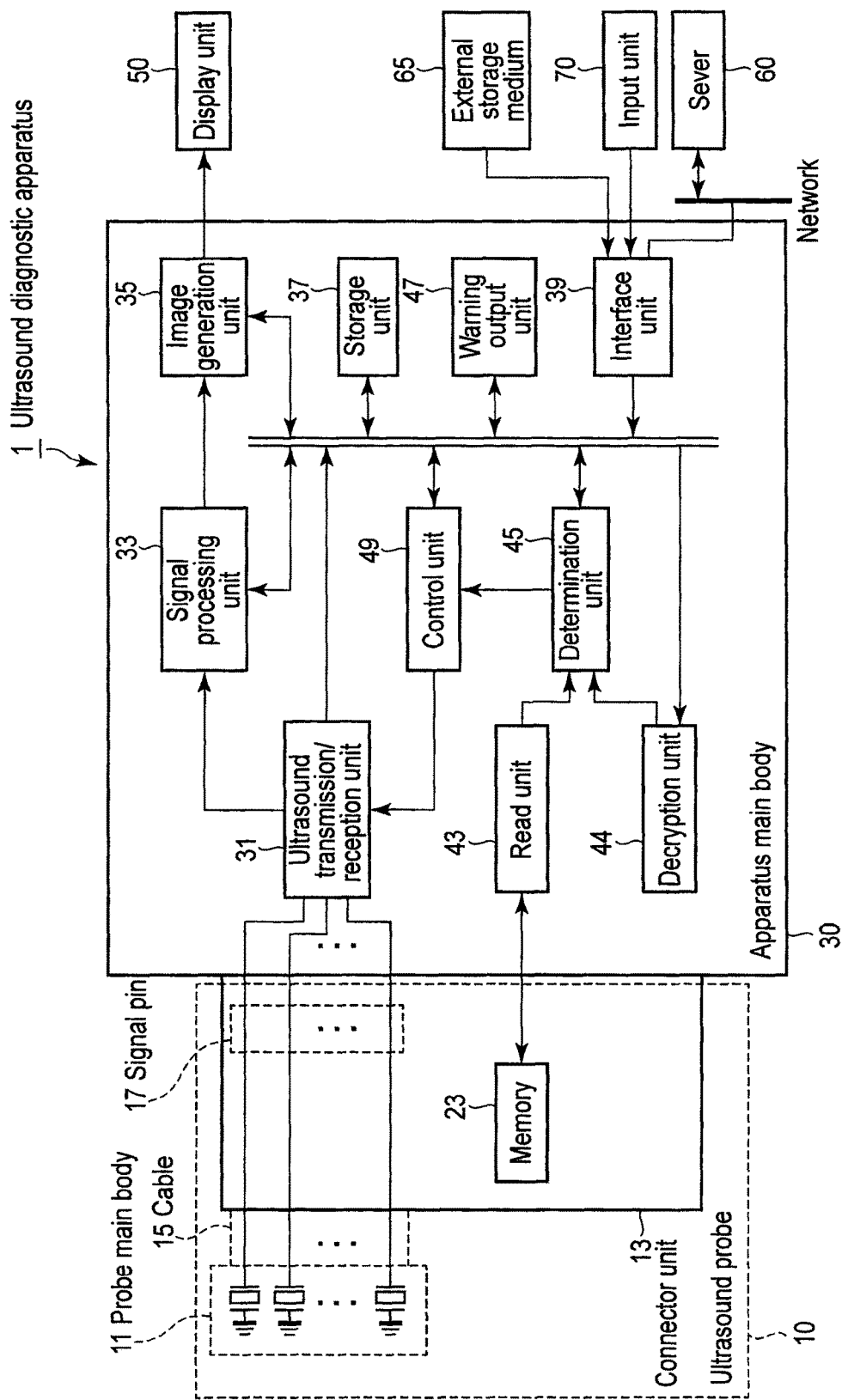
F I G. 5

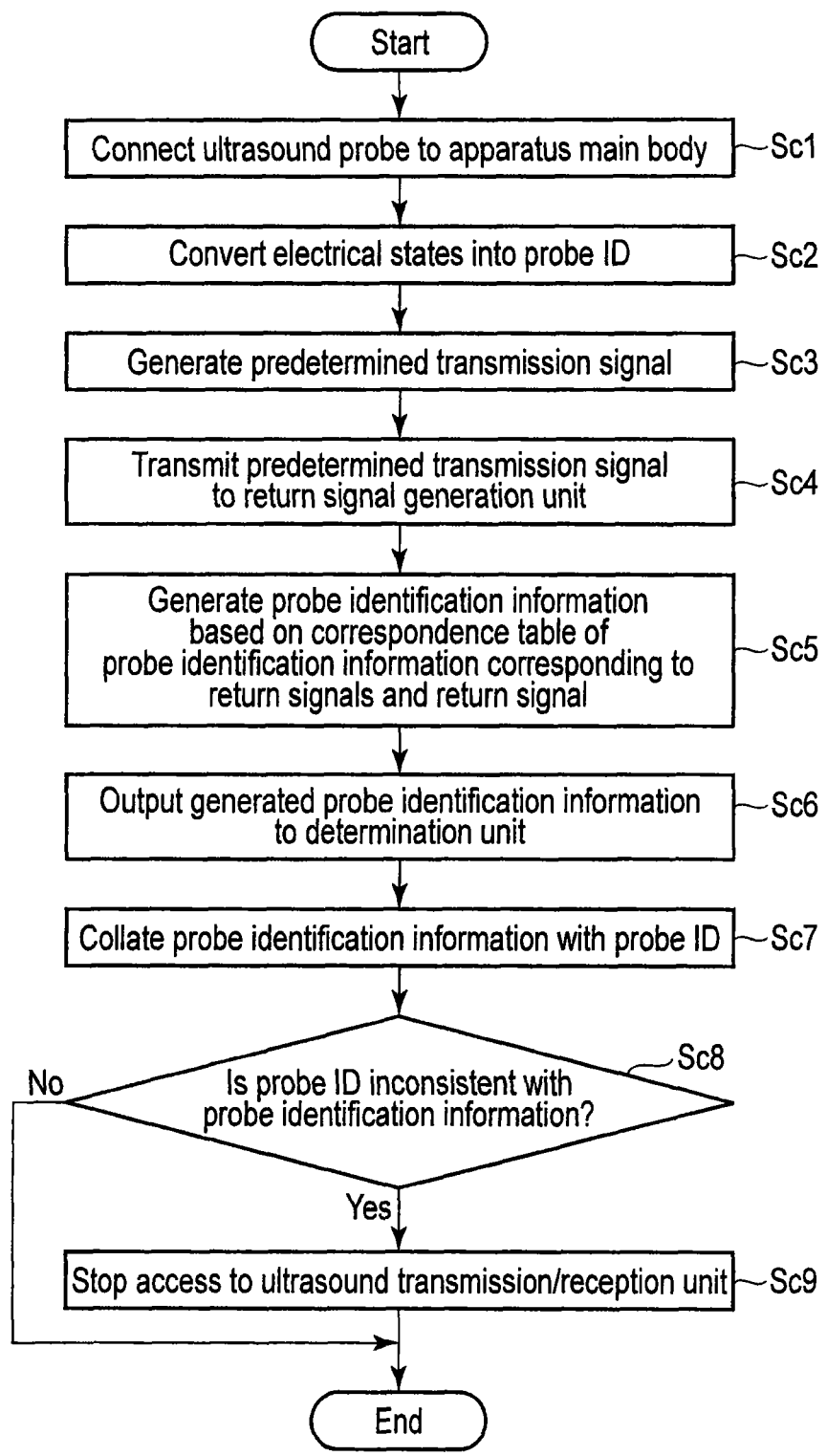
F I G. 8

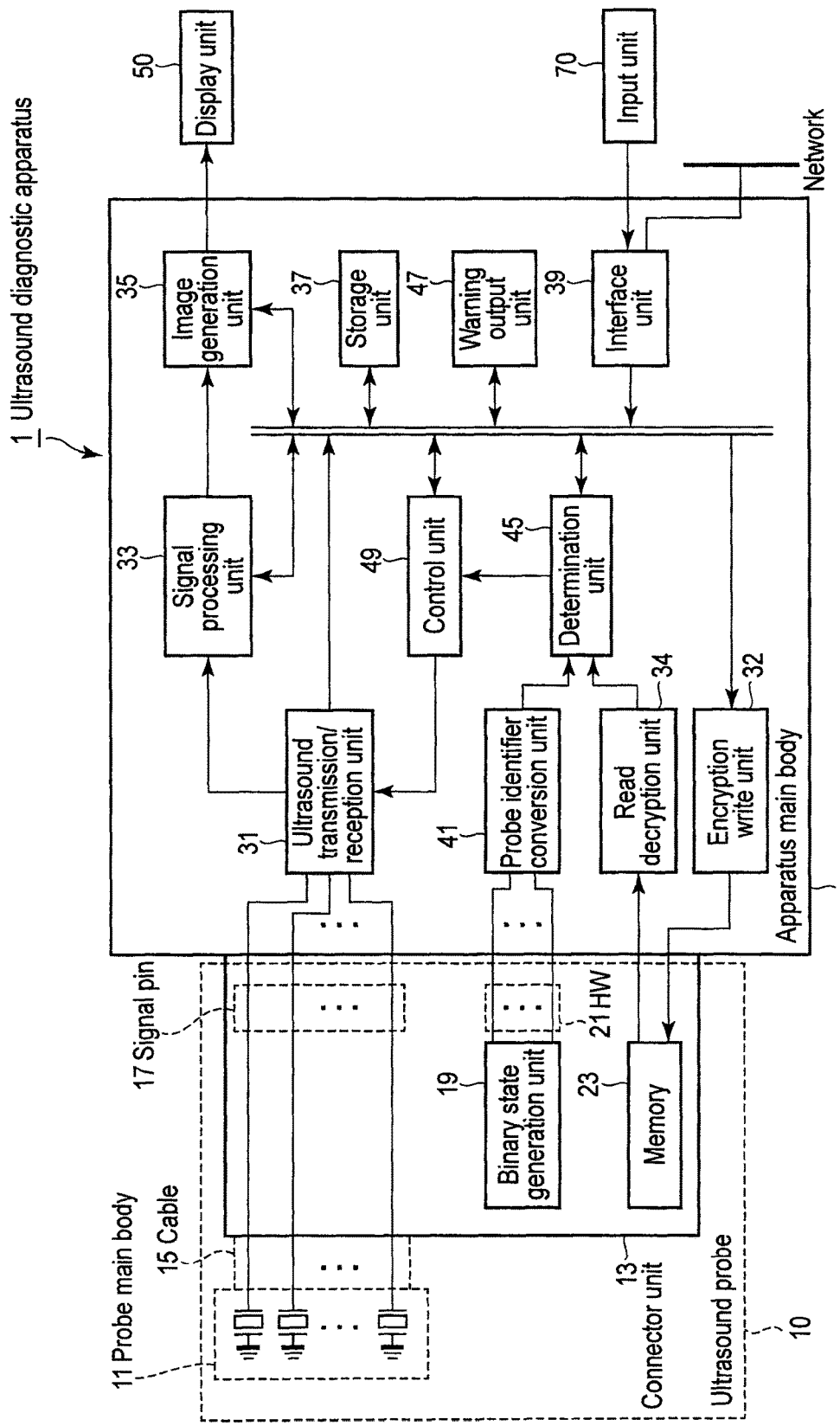
F I G. 9

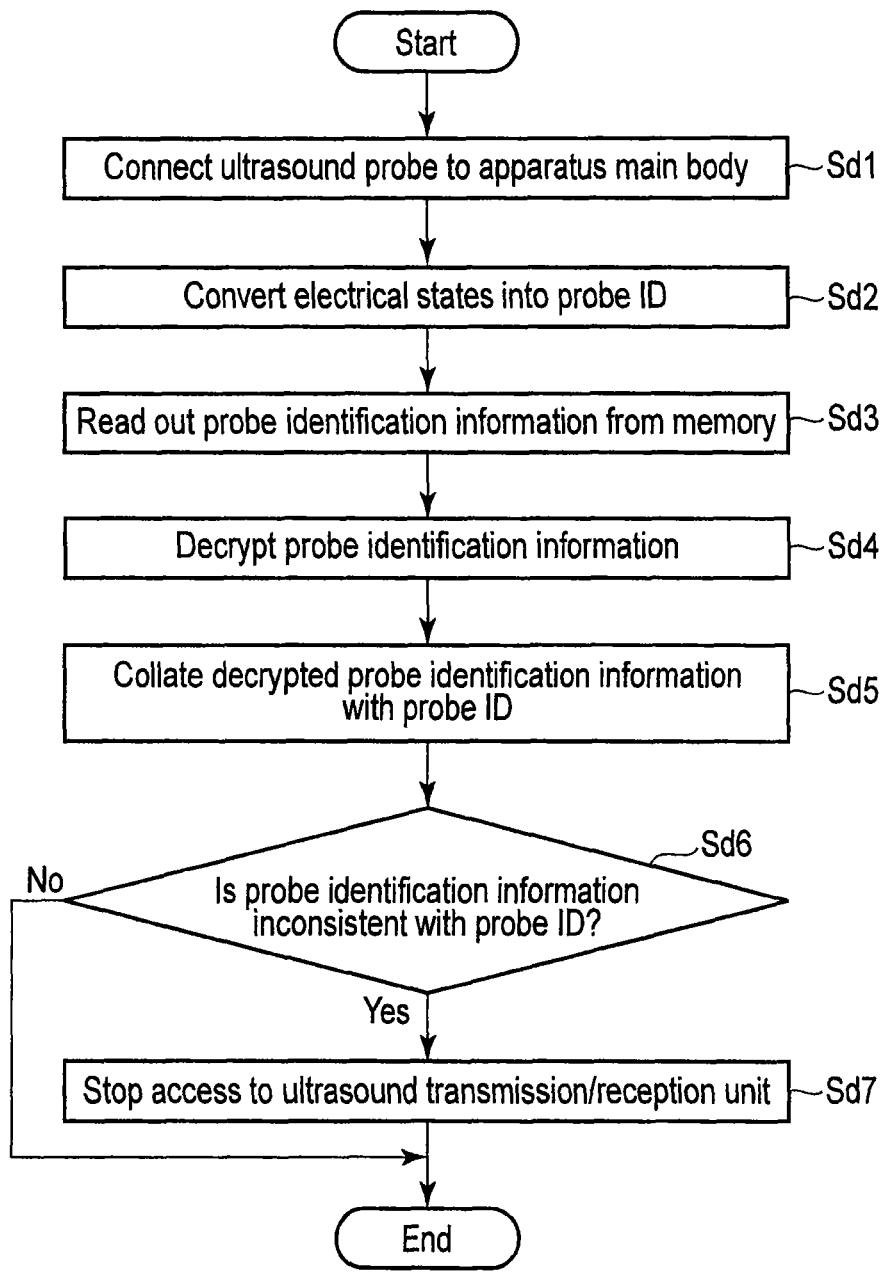
F I G. 10

ULTRASOUND DIAGNOSTIC APPARATUS AND ULTRASOUND PROBE

CROSS-REFERENCE TO RELATED APPLICATIONS

This application is a Continuation application of PCT Application No. PCT/JP2013/067246, filed Jun. 24, 2013 and based upon and claims the benefit of priority from the Japanese Patent Application No. 2012-175203, filed Aug. 7, 2012 and the Japanese Patent Application No. 2013-126815, filed Jun. 17, 2013, the entire contents of all of which are incorporated herein by reference.

FIELD

Embodiments described herein relate generally to an ultrasound diagnostic apparatus and an ultrasound probe.

BACKGROUND

At least one ultrasound probe is connected to the main body of an ultrasound diagnostic apparatus. The connector of the ultrasound probe has a structure configured to be detachably attached to the main body of the ultrasound diagnostic apparatus. An ultrasound probe is selectively used in accordance with a diagnostic target region or application. Different driving schemes are used for ultrasound probes in accordance with forms and applications. For this reason, each ultrasound probe has a probe identifier (identification data to be referred to as ID hereinafter) representing information unique to the ultrasound probe such as various characteristics and a driving scheme of the probe.

The connector of the ultrasound probe has a plurality of hard wires (to be referred to as HWs hereinafter) for making the ultrasound diagnostic apparatus detect a probe ID. A plurality of HWs are respectively connected to a plurality of storage circuits in the connector. Each storage circuit is a circuit which stores a binary signal by, for example, being opened or grounded. A probe ID is set by combining such binary signals.

When an ultrasound probe is connected to the main body of an ultrasound diagnostic apparatus, the ultrasound diagnostic apparatus acquires the probe ID of the ultrasound probe via HWs. The ultrasound diagnostic apparatus identifies the ultrasound probe with the acquired probe ID.

If, however, a probe whose operation is not guaranteed (e.g., a probe from another maker or a pirated probe to be referred to as an unguaranteed probe hereinafter) is erroneously connected to the main body of the ultrasound diagnostic apparatus, the ultrasound diagnostic apparatus erroneously detects the unguaranteed probe. This makes it impossible to execute proper ultrasound probe control, setting, and the like between the ultrasound diagnostic apparatus and the unguaranteed probe. This leads to problems such as a malfunction in the ultrasound diagnostic apparatus, an injury on an object due to the generation of heat by the ultrasound probe, and an diagnostic error.

BRIEF DESCRIPTION OF THE DRAWINGS

FIG. 1 is a block diagram showing an example of the arrangement of an ultrasound diagnostic apparatus according to the first embodiment.

FIG. 5 is a block diagram showing an example of the arrangement of an ultrasound diagnostic apparatus according to the second embodiment.

FIG. 8 is a flowchart showing a procedure for processing concerning a consistency determination function according to the third embodiment.

FIG. 9 is a block diagram showing an example of the arrangement of an ultrasound diagnostic apparatus according to the fourth embodiment.

FIG. 10 is a flowchart showing a procedure for processing concerning a consistency determination function according to the fourth embodiment.

DETAILED DESCRIPTION

Figure 2:
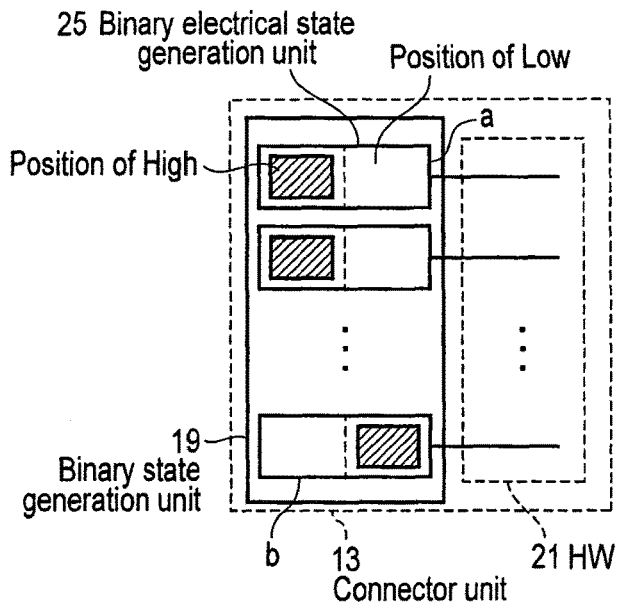
FIG. 2 is a view showing an example of the arrangement of a binary state generation unit in the first embodiment.

An ultrasound diagnostic apparatus according to an embodiment includes an ultrasound probe, a probe identifier conversion unit, a read unit, a determination unit, and a warning output unit.

The ultrasound probe includes a plurality of transducers, a memory to store probe identification information, and a binary state generation unit to generate a binary electrical state corresponding to a probe identifier.

The probe identifier conversion unit converts the electrical state into the probe identifier.

The read unit reads the probe identification information from the memory.

The determination unit determines consistency between the probe identifier after conversion and the probe identification information read from the memory.

The warning output unit outputs a predetermined warning if the determination unit determines inconsistency between the probe identifier after conversion and the probe identification information read from the memory.

The embodiments will be described below with reference to the accompanying drawings. Note that the same reference numerals in the following description denote constituent elements having almost the same functions and arrangements, and a repetitive description will be made only when required.

First Embodiment

FIG. 1 is a block diagram showing an example of the arrangement of an ultrasound diagnostic apparatus according to the first embodiment. As shown in FIG. 1, an ultrasound diagnostic apparatus 1 includes an ultrasound probe 10, an apparatus main body 30, a display unit 50, and an input unit 70 which is connected to the apparatus main body 30 to input various types of instructions, commands, and information from the operator to the apparatus main body 30. A biological signal measurement unit (not shown) typified by an electrocardiograph, phonocardiograph, sphygmograph, or respiration sensor and a network may be connected to the ultrasound diagnostic apparatus 1 via an interface unit 39 to be described later.

The ultrasound probe 10 includes a probe main body 11, a connector unit 13 connected to the apparatus main body 30 of the ultrasound diagnostic apparatus 1, and a cable 15 which electrically connects the probe main body 11 to the connector unit 13.

The probe main body 11 includes a plurality of transducers, matching layers provided on the front surface sides of the plurality of transducers, and backing members provided on the rear surface sides of the plurality of transducers.

The plurality of transducers are lossless acoustic/electric conversion elements such as piezoelectric ceramic elements. A plurality of transducers are arrayed juxtaposed and mounted on the distal end of the ultrasound probe 10. Assume that in the following description, one transducer forms one channel. Each transducer generates an ultrasound in response to the driving pulse supplied from an ultrasound transmission/reception unit 31. When the ultrasound probe 10 transmits an ultrasound to an object, the transmitted ultrasound (to be referred to as the transmission ultrasound hereinafter) is sequentially reflected by a discontinuity surface of acoustic impedance of living tissue in the object. Each transducer receives the reflected ultrasounds and generates an echo signal. The amplitude of this echo signal depends on an acoustic impedance difference on the discontinuity surface, as a boundary, by which the echo signal is reflected. The frequency of the echo signal produced when a transmission ultrasound is reflected by a moving blood flow, the surface of the cardiac wall, or the like is subjected to a frequency shift depending on the velocity component of the moving body (the blood flow and the surface of the cardiac wall) in the ultrasound transmission direction due to the Doppler effect.

The ultrasound probe 10 will be described below as a probe designed to perform two-dimensional scanning with a one-dimensional array. Note that the ultrasound probe 10 may be a mechanical four-dimensional probe which executes three-dimensional scanning by swinging a one-dimensional array in a direction perpendicular to the array direction of a plurality of transducers. In addition, the ultrasound probe 10 is not limited to a mechanical four-dimensional probe, and it is possible to use a two-dimensional array probe.

Matching layers are provided on the front surface sides of a plurality of transducers to improve the efficiency of ultrasound transmission/reception with respect to an object. An acoustic lens (not shown) is provided on the front surface side of each matching layer. The backing members prevent ultrasounds from propagating backward from the transducers.

The connector unit 13 includes a plurality of signal pins 17, a binary state generation unit 19, a hard wire 21 (to be referred to as an HW hereinafter) which electrically connects the binary state generation unit 19 to a probe identifier conversion unit 41 (to be described later) of the apparatus main body 30, a memory 23, and a memory connection pin for electrically connecting the memory 23 to a read unit 43 (to be described later) of the apparatus main body 30.

When the ultrasound probe 10 is connected to the apparatus main body 30, each of the plurality of signal pins 17 is electrically connected to the ultrasound transmission/reception unit 31 in the apparatus main body 30 via a wiring. When the ultrasound probe 10 is connected to the apparatus main body 30, the HW 21 is electrically connected to the probe identifier conversion unit 41 in the apparatus main body 30 via a wiring. When the ultrasound probe 10 is connected to the apparatus main body 30, the memory connection pin is electrically connected to the read unit 43 in the apparatus main body 30 via a wiring.

The cable 15 includes a plurality of wirings which electrically connect the plurality of signal pins 17 of the connector unit 13 to the probe main body 11. The plurality of wirings each are coated with an insulator for insulation.

The binary state generation unit 19 generates a binary electrical state corresponding to the probe identifier (identification data to be referred to as a probe ID hereinafter) of the ultrasound probe 10. Note that a serial number may be generated instead of the probe ID. FIG. 2 is a block diagram showing an example of the arrangement of the binary state generation unit 19. As shown in FIG. 2, the binary state generation unit 19 includes a plurality of binary electrical state generation units 25 electrically connected to the plurality of HWs 21, respectively. Each binary electrical state generation unit 25 generates a binary electrical state by, for example, a switch. More specifically, the binary electrical state generation unit 25 generates a binary electrical state (high (H) or low (L)) by grounding or opening the HW 21. A probe ID is expressed by a combination pattern of binary electrical states (H and L). Referring to FIG. 2, the electrical state indicated by "a" in the binary electrical state generation units 25 is "H", whereas the electrical state indicated by "b" in the binary electrical state generation units 25 is "L".

The memory 23 stores information for identifying the type of ultrasound probe 10 (to be referred to as probe identification information hereinafter). Probe identification information is permanent information such as the serial number, the probe ID, the individual information of the ultrasound probe 10, or the like at the time of shipment of the ultrasound probe 10 or at the time of installation of the ultrasound diagnostic apparatus 1. Note that the information stored in the memory 23 is not limited to the fixed information described above. That is, the memory 23 may store, for example, information which changes in accordance with the use of the ultrasound probe 10, e.g., the use history information of the ultrasound probe 10 (to be referred to as probe use history information hereinafter). Probe use history information is information concerning the use history of the ultrasound probe 10, e.g., the use time, use date, and the like of the ultrasound probe 10. Note that a storage unit 37 (to be described later) may store probe use history information. The probe use history information is updated when it is stored in the memory 23 or the storage unit 37.

Figure 3:
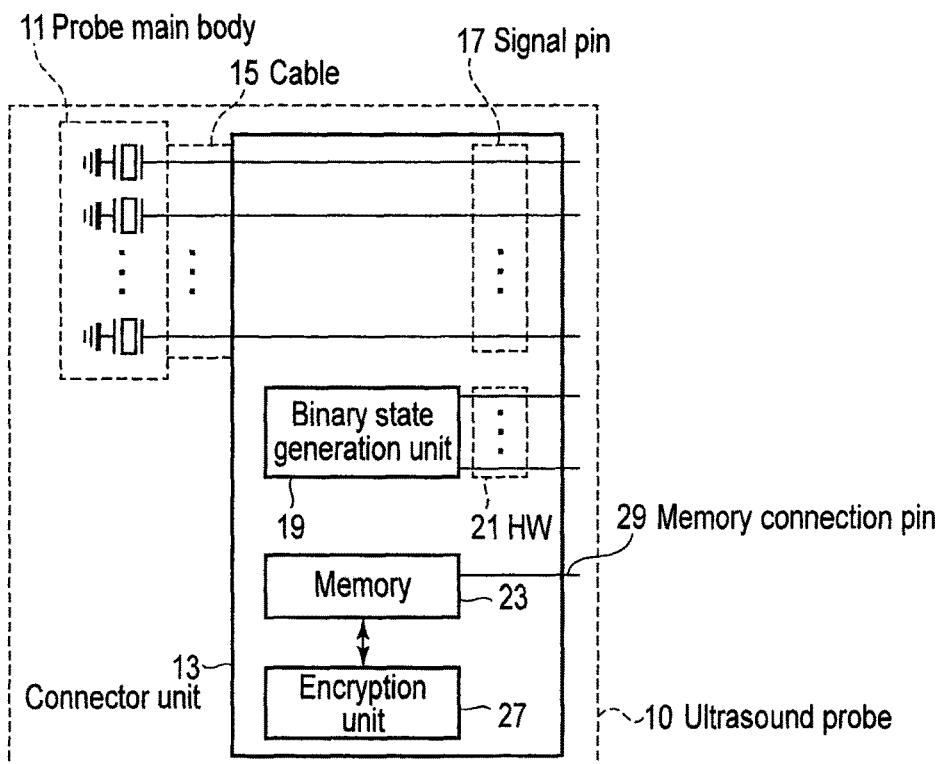
FIG. 3 is a view showing a modification of the arrangement of an ultrasound probe in the first embodiment.

In addition, probe identification information may be encrypted and stored in the memory 23. At this time, the connector unit 13 is provided with an encryption unit which encrypts probe identification information. Note that the encryption unit may be provided for the apparatus main body 30. FIG. 3 shows the arrangement of a modification of the arrangement of the ultrasound probe 10. The connector unit 13 includes an encryption unit 27.

The encryption unit 27 encrypts probe identification information based on, for example, probe use history information. The encryption unit 27 causes the memory 23 to store an encryption key such as probe use history information used for encryption. The apparatus main body 30 supplies power for the encryption unit 27 via the memory 23 and a memory connection pin 29. Note that a power supply may be mounted on the connector unit 13.

Note that the encryption unit 27 may, for example, encrypt, as hardware, probe identification information. For example, the encryption unit 27 may incorporate a TPM (Trusted Platform Module) as hardware. For example, the apparatus main body 30 supplies power for the encryption unit 27 as hardware via the memory 23 and the memory connection pin 29 in response to the connection of the ultrasound probe 10 to the apparatus main body 30. At this time, the encryption unit 27 stores a private key for encrypting probe identification information and a public key for decrypting encrypted probe identification information. The encryption unit 27 encrypts probe identification information with a private key, as needed.

The apparatus main body 30 includes the ultrasound transmission/reception unit 31, a signal processing unit 33, an image generation unit 35, the storage unit 37, the interface unit 39, the probe identifier conversion unit 41, the read unit 43, a determination unit 45, a warning output unit 47, and a control unit 49. The ultrasound transmission/reception unit 31 includes an ultrasound transmission unit and an ultrasound reception unit (neither of which is shown).

The ultrasound transmission unit includes a pulse generator, transmission delay circuit, and pulser circuit (none of which are shown). The ultrasound transmission unit applies voltage pulses to the plurality of transducers, respectively, under the control of the control unit 49 (to be described later). The ultrasound transmission unit transmits ultrasounds to an object via transducers upon application of voltage pulses.

The pulse generator repeatedly generates rate pulses for the formation of transmission ultrasounds at a predetermined rate frequency fr Hz (period: 1/fr sec). The generated rate pulses are distributed to channel counts and sent to the transmission delay circuit. The transmission delay circuit gives each rate pulse a delay time (to be referred to as a transmission delay time hereinafter) necessary to focus a transmission ultrasound into a beam and determine transmission directivity for each of the plurality of channels. The storage unit 37 (to be described later) stores the transmission direction or transmission delay time of transmission ultrasounds (to be referred to as a transmission delay pattern hereinafter). The control unit 49 (to be described later) refers to the transmission delay pattern stored in the storage unit 37 at the time of transmission of ultrasounds. The pulser circuit applies a voltage pulse (driving signal) to each of the plurality of transducers of the ultrasound probe 10 at the timing based on this rate pulse. With this operation, an ultrasound beam is transmitted to the object.

The ultrasound reception unit includes a preamplifier, analog to digital (to be referred to as A/D hereinafter) converter, reception delay circuit, and adder (none of which are shown). The ultrasound reception unit generates reception signals based on echo signals from an object which are received via the ultrasound probe 10 under the control of the control unit 49 (to be described later).

The preamplifier amplifies an echo signal received from an object via the ultrasound probe 10 for each channel. The A/D converter converts each amplified echo signal into a digital signal. The reception delay circuit gives the reception echo signals converted into digital signals delay times (to be referred to as reception delay times hereinafter) required to determine reception directivity. The storage unit 37 (to be described later) stores the reception direction or reception delay time of an echo signal (to be referred to as a reception delay pattern hereinafter). The control unit 49 (to be described later) refers to the reception delay pattern stored in the storage unit 37. The adder adds a plurality of echo signals given the delay times. With this addition, the ultrasound transmission/reception unit generates a reception signal (to be also referred to as an RF (radiofrequency) signal) with a reflection component from a direction corresponding to the reception directivity being enhanced. The transmission directivity and the reception directivity determine the comprehensive directivity of ultrasound transmission/reception. This comprehensive directivity determines an ultrasound beam (so-called "ultrasound scanning line").

The signal processing unit 33 includes a B-mode processing unit and a Doppler processing unit (neither of which is shown). The signal processing unit 33 generates at least one of B-mode data and Doppler data based on the reception signal output from the ultrasound transmission/reception unit 31.

The B-mode processing unit includes an envelope detector and a logarithmic converter (neither of which is shown). The envelope detector performs envelope detection of the reception signal output from the ultrasound transmission/reception unit 31. The envelope detector outputs the envelope-detected signal to the logarithmic converter (to be described later). The logarithmic converter relatively enhances a weak signal by logarithmically converting the envelope-detected signal. The B-mode processing unit generates a signal value (B-mode data) for each depth on each scanning line or in each ultrasound transmission/reception based on the signal enhanced by the logarithmic converter.

Note that if the ultrasound probe 10 is a mechanical four-dimensional probe or two-dimensional array probe, the B-mode processing unit may generate three-dimensional B-mode data having a plurality of signal values respectively arrayed in the azimuth direction, elevation direction, and depth direction (to be referred to as the range direction hereinafter) in a scanned region. The range direction is the depth direction on a scanning line. The azimuth direction is, for example, an electronic scanning direction along the array direction of one-dimensional ultrasound transducers. The elevation direction is the mechanical swinging direction of the one-dimensional ultrasound transducers. Note that three-dimensional B-mode data may be data obtained by arraying a plurality of pixel values, a plurality of luminance values, or the like in the azimuth direction, elevation direction, and range direction, respectively, along scanning lines. In addition, three-dimensional B-mode data may be data concerning a region of interest (to be referred to as an ROI hereinafter) set in advance in a scanned region. The B-mode processing unit may generate volume data instead of three-dimensional B-mode data. The date generated by the B-mode processing unit will be collectively referred to as B-mode data.

The Doppler processing unit includes a mixer, low pass filter (to be referred to as an LPF hereinafter), and velocity/variance/power computation device (none of which are shown). The mixer multiplies the reception signal output from the ultrasound transmission/reception unit 31 by a reference signal having a frequency $f_0$ equal to the transmission frequency. This multiplication obtains a signal having a component with a Doppler shift frequency $f_d$ and a signal having a frequency component of $(2f_0+f_d)$. The LPF removes a signal of a high-frequency component $(2f_0+f_d)$ from a signal having two types of frequency components from the mixer. The Doppler processing unit generates a Doppler signal having the component with the Doppler shift frequency $f_d$ by removing the signal of the high-frequency component $(2f_0+f_d)$.

Note that the Doppler processing unit may use a quadrature detection scheme to generate Doppler signals. In this case, the Doppler processing unit performs quadrature detection to convert a reception signal (RF signal) into an IQ signal. The Doppler processing unit generates a Doppler signal having the Doppler shift frequency $f_d$ by performing complex Fourier transform for the IQ signal. Doppler signals are, for example, Doppler components originating from a blood flow, tissue, and contrast medium.

The velocity/variance/power computation device includes an MTI (Moving Target Indicator) filter, LPF filter, and autocorrelation computation device (none of which are shown). Note that a cross-correlation computation device may be used instead of the autocorrelation computation device. The MTI filter removes a Doppler component (a clutter component) due to the respiratory movement or pulsatory movement of an organ or the like from a generated Doppler signal. The MTI filter is used to extract a Doppler component concerning a blood flow (to be referred to as a blood flow Doppler component hereinafter) from a Doppler signal. The LPF is used to extract a Doppler component concerning the movement of a tissue (to be referred to as a tissue Doppler component hereinafter) from a Doppler signal.

The autocorrelation computation device calculates the autocorrelation value between a blood flow Doppler component and a tissue Doppler component. The autocorrelation computation device calculates the average flow velocity value, a variance, the reflection intensity (power) of the Doppler signal, and the like on the basis of the calculated autocorrelation value. The velocity/variance/power computation device generates color Doppler data from the average velocity value, the variance, the reflection intensity of the Doppler signal, and the like based on a plurality of Doppler signals. Doppler signals and color Doppler data will be collectively referred to as Doppler data hereinafter.

The image generation unit 35 includes a digital scan converter (to be referred to as a DSC hereinafter), image memory, and image combining unit (none of which are shown). The image generation unit 35 executes coordinate conversion processing (resampling) for the DSC. Coordinate conversion processing is to convert, for example, a scanning line signal string for ultrasound scanning, which is formed from, for example, B-mode data and Doppler data, into a scanning line signal string in a general video format typified by a TV format. The image generation unit 35 generates an ultrasound image as a display image by coordinate conversion processing. More specifically, the image generation unit 35 generates a B-mode image based on B-mode data. The image generation unit 35 generates a Doppler image such as an average velocity image, variance image, or power image based on Doppler data.

The image memory stores data (to be referred to as image data hereinafter) which corresponds a generated ultrasound image (a B-mode image, average velocity image, variance image, or power image). The image data stored in the image memory is read out in accordance with the instruction issued by the operator via the input unit 70 (to be described later). The image memory is, for example, a memory which stores ultrasound images corresponding to a plurality of frames immediately before freezing. Continuously displaying (cine-displaying) the images stored in this cine memory can also display a moving ultrasound image on the display unit 50 (to be described later).

The image combining unit combines an ultrasound image with the character information of various parameters, scale marks, and the like. The image combining unit outputs the combined ultrasound image to the display unit 50.

The storage unit 37 stores pluralities of reception delay patterns and transmission delay patterns with different focus depths, control programs for the ultrasound diagnostic apparatus 1, a diagnostic protocol, various data groups such as transmission/reception conditions, diagnosis information (patient ID, findings by doctors, and the like), the reception signals generated by the ultrasound transmission/reception unit 31, the B-mode data, Doppler data, B-mode images, average velocity images, variance images, and power images generated by the signal processing unit 33, and the like. Note that the image memory may be provided in the storage unit 37.

The storage unit 37 stores list information concerning a plurality of probe identifiers respectively corresponding to a plurality of ultrasound probes. The storage unit 37 stores a plurality of scan schemes respectively corresponding to a plurality of probe identifiers. The storage unit 37 stores a plurality of image processing schemes respectively corresponding to a plurality of probe identifiers.

The interface unit 39 is an interface concerning the input unit 70, a network, an external storage device (not shown), and a biological signal measurement unit (not shown). Data such as ultrasound images, analysis results, and the like obtained by the apparatus main body 30 can be transferred to other apparatuses via the interface unit 39 and the network. The interface unit 39 can also download the medical images concerning the object which are acquired by other medical image diagnostic apparatuses (not shown) via the network.

The probe identifier conversion unit 41 converts the electrical states stored in the binary state generation unit 19 into a probe ID. The probe identifier conversion unit 41 outputs the generated probe ID to the determination unit 45 (to be described later). More specifically, when the connector unit 13 of the ultrasound probe 10 is connected to the apparatus main body 30, the probe identifier conversion unit 41 acquires binary electrical states via the HWs 21. The probe identifier conversion unit 41 converts the acquired electrical states into a probe ID.

When the connector unit 13 of the ultrasound probe 10 is connected to the apparatus main body 30, the read unit 43 reads out the probe identification information stored in the memory 23. The read unit 43 outputs the readout probe identification information to the determination unit 45 (to be described later).

The determination unit 45 determines the consistency between the probe ID and the probe identification information. The determination unit 45 outputs the consistency determination result to the warning output unit 47 and the control unit 49. More specifically, the determination unit 45 collates the probe ID with the probe identification information. More specifically, for example, the determination unit 45 extracts a probe ID from the probe identification information. The determination unit 45 determines whether the extracted probe ID matches the generated probe ID. Note that the control unit 49 (to be described later) can execute the processing performed by the determination unit 45 as software.

The warning output unit 47 outputs a predetermined warning if the determination result output from the determination unit 45 indicates inconsistency. The predetermined warning is a display form including, for example, a red indication, blinking, or an error message. Note that the warning output unit 47 may output a predetermined warning sound. The warning output unit 47 may also output information concerning a predetermined warning to the display unit 50 to make it output a predetermined warning (to be described later).

The control unit 49 reads out a transmission delay pattern, reception delay pattern, and control program from the storage unit 37 based on the selection between the B mode and the Doppler mode, frame rate, scan depth, and transmission start/end which are input by the operator via the input device

70. The control unit 49 controls the apparatus main body 30 in accordance with these readout data.

If the determination result output from the determination unit 45 indicates inconsistency, the control unit 49 controls the ultrasound transmission/reception unit 31 so as not to execute ultrasound transmission/reception. More specifically, the control unit 49 stops access to the ultrasound transmission/reception unit 31 if the determination result output from the determination unit 45 indicates inconsistency. If the determination result output from the determination unit 45 indicates consistency, the control unit 49 specifies the type, characteristics, driving scheme, scan scheme, image processing scheme, and the like of the ultrasound probe 10 connected to the apparatus main body 30 by using the probe ID and the probe identification information in the list information. The control unit 49 controls the ultrasound transmission/reception unit 31 to execute ultrasound transmission/reception by using the connected ultrasound probe 10 in accordance with the specified type, characteristics, driving scheme, scan scheme, and the like. The control unit 49 controls the signal processing unit 33, the image generation unit 35, and the like in accordance with the specified image processing scheme. The control unit 49 updates the probe use history information in response to the end of the examination on the object.

The display unit 50 displays ultrasound images such as a B-mode image and a Doppler image based on outputs from the image generation unit 35. Note that the display unit 50 may execute adjustments concerning brightness, contrast, dynamic range, γ correction, and the like and color mapping. In addition, the display unit 50 may display a predetermined warning such as an error message based on an output from the warning output unit 47.

The input device 70 is connected to the interface unit 39 and inputs various instructions, commands, information, selections, and settings from the operator to the apparatus main body 30. The input device 70 includes input devices such as a trackball, switch buttons, mouse, and keyboard (none of which are shown). The input device detects the coordinates of a cursor displayed on the display screen, and outputs the detected coordinates to the control unit 49. Note that the input device may be a touch command screen provided to cover the display screen. In this case, the input device 70 detects touched and designated coordinates by a coordinate reading principle such as an electromagnetic induction scheme, magnetostriction scheme, or a pressure-sensitive scheme, and outputs the detected coordinates to the control unit 49. When, for example, the operator operates the end button or freeze button of the input device 70, the ultrasound transmission/reception is terminated, and the apparatus main body 30 is set in a pause state.

(Consistency Determination Function)

The consistency determination function is a function concerning a procedure for determining the consistency between the probe ID converted by the probe identifier conversion unit 41 and the probe identification information read out from the read unit 43. Processing concerning the consistency determination function (to be referred to as consistency determination processing hereinafter) will be described below.

Figure 4:
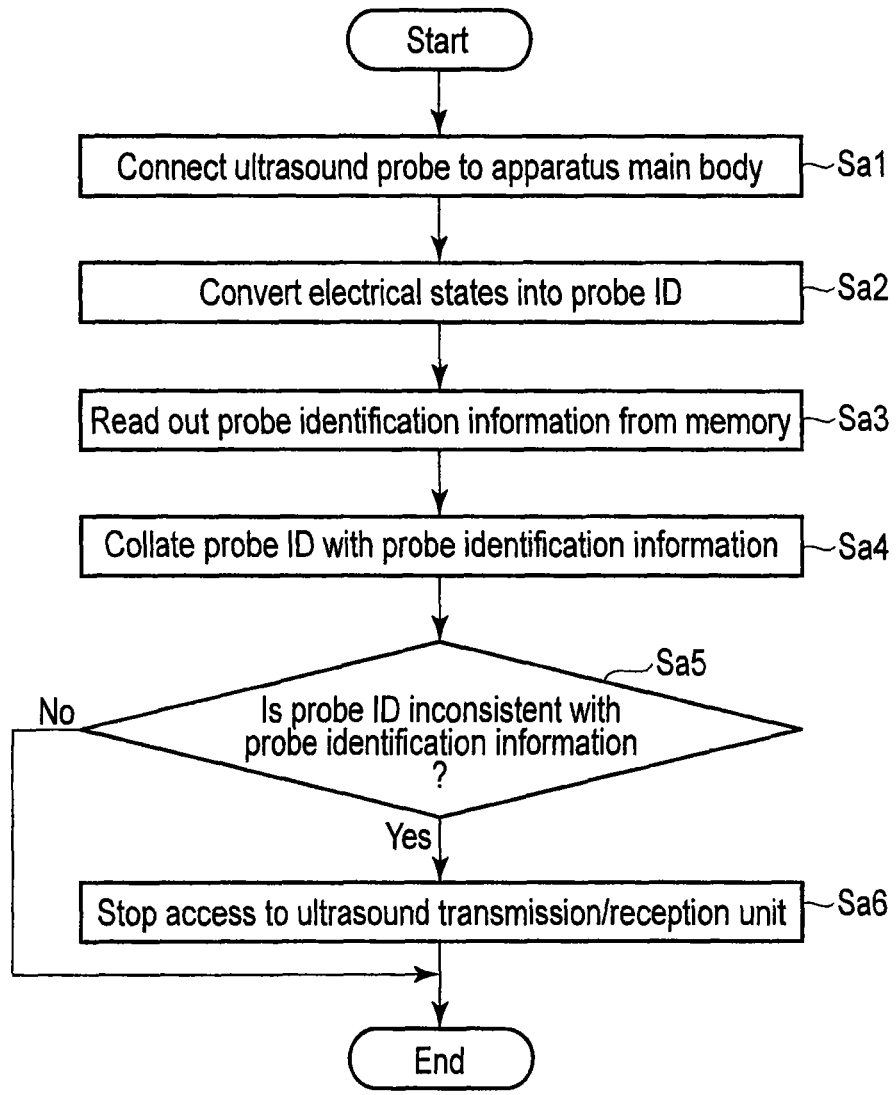
FIG. 4 is a flowchart showing a procedure for processing concerning a consistency determination function according to the first embodiment.

FIG. 4 is a flowchart showing a procedure for consistency determination processing. The ultrasound probe 10 is connected to the apparatus main body 30 (step Sa1). The electrical states in the binary state generation unit 19 are converted into a probe ID (step Sa2). The converted probe ID is output to the determination unit 45. Probe identification information is read out from the memory 23 (step Sa3).

The readout probe identification information is output to the determination unit 45. The determination unit 45 collates the probe ID with the probe identification information (step Sa4). If the probe ID is consistent with the probe identification information (step Sa5), the ultrasound transmission/reception unit 31 is controlled to execute ultrasound transmission/reception. If the probe ID is inconsistent with the probe identification information (step Sa5), access to the ultrasound transmission/reception unit 31 is stopped (step Sa6). At this time, the warning output unit 47 outputs a predetermined warning.

(Modification)

This modification differs from the first embodiment in that it is configured to determine whether a probe ID and probe identification information each are included in list information.

The determination unit 45 determines whether the probe ID is included in the list information. A determination result concerning the presence/absence of a probe ID in list information will be referred to as the first determination result hereinafter. The determination unit 45 determines whether probe identification information is included in the list information. A determination result concerning the presence/absence of probe identification information in list information will be referred to as the second determination result hereinafter. The determination unit 45 outputs the first and second determination results to the warning output unit 47 and the control unit 49. The determination unit 45 can also determine the consistency between a probe ID and probe identification information as in the first embodiment.

More specifically, the determination unit 45 reads out list information from the storage unit 37. The determination unit 45 then extracts a plurality of probe IDs from the readout list information. The determination unit 45 collates each of the extracted probe IDs with the probe identifier converted by the probe identifier conversion unit 41. In addition, the determination unit 45 collates each of the extracted probe IDs with the readout probe identification information. The determination unit 45 outputs the collation results (first and second determination results) to the warning output unit 47 and the control unit 49.

The warning output unit 47 outputs a predetermined warning if at least one of the first and second determination results indicates inconsistency. Note that the warning output unit 47 may transmit the first and second determination results to, for example, a serviceman (predetermined operator) via the interface unit 39 and a network in accordance with a predetermined warning output. If probe identification information is lost from the memory 23, a predetermined operator or the like may rewrite or update information as needed.

More specifically, if the first determination result indicates inconsistency and the second determination result indicates consistency, the warning output unit 47 outputs information concerning a predetermined warning (e.g., the possibility of HW disconnection or erroneous insertion (a connector is inversely inserted into the apparatus main body)) or the like to the display unit 50. If the first determination result indicates consistency and the second determination result indicates inconsistency, the warning output unit 47 outputs information concerning a predetermined warning (e.g., the possibility that a connected ultrasound probe may be an unauthorized product) to the display unit 50.

The control unit 49 controls the ultrasound transmission/reception unit 31 so as not to perform ultrasound transmission/reception, if at least one of the first and second determination results indicates inconsistency. More specifically, if at least one of the first and second determination results indicates inconsistency, the control unit 49 stops access to the ultrasound transmission/reception unit 31. If both the first and second determination results indicate consistency, the control unit 49 specifies the type, characteristics, driving scheme, scan scheme, image processing scheme, and the like of the ultrasound probe 10 connected to the apparatus main body 30 by using the probe ID and the probe identification information in the list information. The control unit 49 controls the ultrasound transmission/reception unit 31 to execute ultrasound transmission/reception by using the connected ultrasound probe 10 in accordance with the specified type, characteristics, driving scheme, scan scheme, and the like. The control unit 49 controls the signal processing unit 33, the image generation unit 35, and the like in accordance with the specified image processing scheme.

According to the above arrangement, the following effects can be obtained.

According to the ultrasound diagnostic apparatus 1 of this embodiment, it is possible to determine consistency between the probe ID obtained by converting the electrical states stored in the binary state generation unit 19 provided in the ultrasound probe 10 and the probe identification information stored in the memory 23. If the probe ID is inconsistent with the probe identification information, it is possible to stop access to the ultrasound transmission/reception unit 31. In addition, it is possible to output a predetermined warning such as an error message. Furthermore, it is possible to display an error message or the like on the display unit 50. This embodiment can also detect a contact failure between the connector unit 13 and the apparatus main body 30. That is, if a contact failure occurs, it is not possible to determine consistency between the probe ID and the probe identification information. For this reason, if no probe ID is generated or no probe identification information is read, it is possible to detect a contact failure between the connector unit 13 and the apparatus main body 30.

According to this modification, it is possible to determine whether the probe ID obtained by converting the electrical states generated by the binary state generation unit 19 and the probe identification information read out from the read unit 43 each are included in the list information stored in the storage unit 37.

According to this modification, this makes it possible to output, to the display unit 50, information concerning a predetermined warning such as the possibility of HW disconnection, the possibility of connection of the ultrasound probe 10 to the apparatus main body 30 in a wrong direction, or the possibility of tampering of binary electrical states, if the probe ID is not included in the list information. In addition, according to the modification, it is possible to output, to the display unit 50, information concerning a predetermined warning such as the possibility that the connected ultrasound probe is an unauthorized product, if the probe ID is included in the list information and the probe identification information is not included in the list information. Furthermore, as in the first embodiment, it is possible to determine consistency between a probe ID and probe identification information. According to this modification, it is also possible to detect a contact failure between the connector unit 13 and the apparatus main body 30 (e.g., a contact failure between the binary state generation unit 19 and the probe identifier conversion unit 41 due to HW disconnection or a contact failure between the memory 23 and the read unit 43). As described above, according to the modification, it is possible to make a double check by determining consistency between list information and a probe ID and determining consistency between the list information and probe identification information.

As described above, even if an unguaranteed probe is erroneously connected to the apparatus main body 30 of the ultrasound diagnostic apparatus 1, it is possible to solve the problem of erroneous recognition of the unguaranteed probe. Even if an unguaranteed probe is erroneously connected to the apparatus main body 30, this makes it possible to avoid possibilities such as a malfunction in the ultrasound diagnostic apparatus 1 due to the inability to perform proper control and setting on the ultrasound probe, an injury on an object due to the generation of heat by the ultrasound probe, and an diagnostic error. As described above, according to the ultrasound diagnostic apparatus 1, it is possible to ensure safety for an object and the ultrasound diagnostic apparatus 1 and prevent diagnostic errors.

Second Embodiment

The second embodiment differs from the first embodiment in that it is configured to determine consistency between the probe identification information stored in a memory 23 and the probe identification information list stored in an external storage medium or server.

FIG. 5 is a block diagram showing an example of the arrangement of an ultrasound diagnostic apparatus 1 according to the second embodiment. As shown in FIG. 5, an apparatus main body 30 includes a decryption unit 44. In addition, as shown in FIG. 5, an interface unit 39 is connected to a server 60 via a network. Note that an external storage medium 65 may be connected to the interface unit 39, as shown in FIG. 5.

The server 60 or external storage medium 65 stores a probe identification information list encrypted by a predetermined method. The probe identification information list is a list of probe identification information concerning each of a plurality of different types of ultrasound probes.

The decryption unit 44 acquires an encryption key and an encrypted probe identification information list from the server 60 or external storage medium 65 connected via the interface unit 39. The decryption unit 44 decrypts the encrypted probe identification information list by using the encryption key. The decryption unit 44 outputs the decrypted probe identification information list to a determination unit 45.

The determination unit 45 determines consistency between probe identification information and a probe identification information list. The determination unit 45 outputs a consistency determination result to a warning output unit 47 and a control unit 49 (both of which will be described later). More specifically, the determination unit 45 collates the probe identification information with the probe identification information list. That is, the determination unit 45 determines whether the probe identification information matches one piece of probe identification information in the probe identification information list.

(Consistency Determination Function)

The consistency determination function is a function concerning a procedure for determining consistency between the probe identification information read out from a read unit 43 and the probe identification information list decrypted by the decryption unit 44. Processing concerning the consistency determination function (to be referred to as consistency determination processing hereinafter) will be described below.

Figure 6:
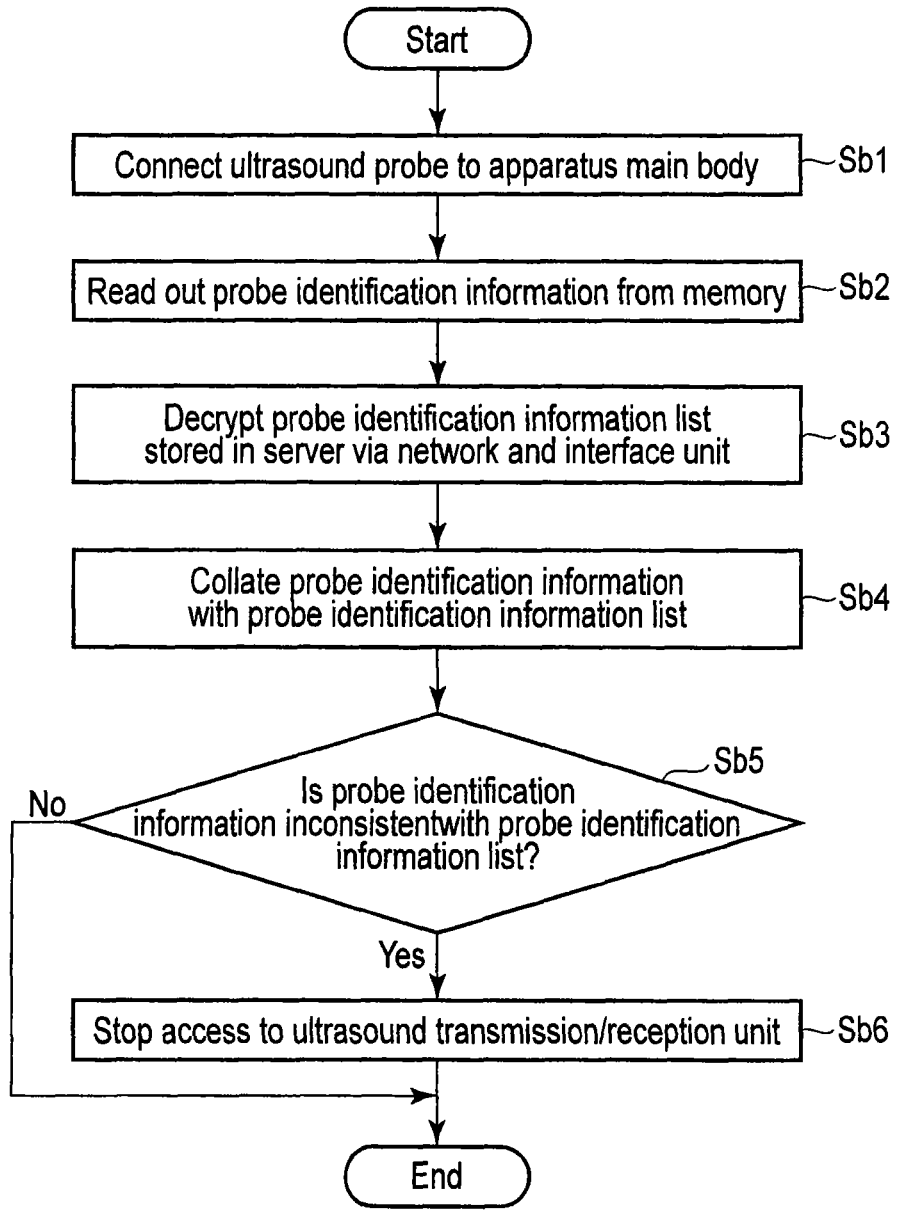
FIG. 6 is a flowchart showing a procedure for processing concerning a consistency determination function according to the second embodiment.

FIG. 6 is a flowchart showing a procedure for consistency determination processing. An ultrasound probe 10 is connected to the apparatus main body 30 (step Sb1). The apparatus reads out probe identification information from the memory 23 (step Sb2). The apparatus outputs the readout probe identification information to the determination unit 45. The apparatus decrypts the probe identification information list stored in the server 60 and encrypted by using the encryption key via the interface unit 39 (step Sb3). If the apparatus cannot be connected to a network, the external storage medium 65 storing the encrypted probe identification information list may be connected to the apparatus main body 30 via the interface unit 39. The apparatus outputs the decrypted probe identification information list to the determination unit 45. The determination unit 45 collates the probe identification information with the probe identification information list (step Sb4). If the probe identification information matches one piece of probe identification information in the probe identification information list (step Sb5), the apparatus controls an ultrasound transmission/reception unit 31 to execute ultrasound transmission/reception. If the probe identification information matches none of all the pieces of probe identification information in the probe identification information list (step Sb5), the apparatus stops access to the ultrasound transmission/reception unit 31 (step Sb6). At this time, the warning output unit 47 may output a predetermined warning.

According to the above arrangement, the following effects can be obtained.

The ultrasound diagnostic apparatus 1 of this embodiment can determine consistency between the probe identification information stored in the memory 23 and the probe identification information list stored in the server 60 or external storage medium 65. If the probe identification information matches none of all the pieces of probe identification information in the probe identification information list, the apparatus can stop access to the ultrasound transmission/reception unit 31. In addition, the apparatus can output a predetermined warning such as an error message. Furthermore, the apparatus can display an error message or the like on the display unit 50. The probe identification information list is encrypted by a predetermined method.

As described above, even if an unguaranteed probe is erroneously connected to the apparatus main body 30 of the ultrasound diagnostic apparatus 1, it is possible to solve the problem of erroneous recognition of the unguaranteed probe. Even if an unguaranteed probe is erroneously connected to the apparatus main body 30, this makes it possible to avoid possibilities such as a malfunction in the ultrasound diagnostic apparatus 1 due to the inability to perform proper control and setting on the ultrasound probe, an injury on an object due to the generation of heat by the ultrasound probe, and an diagnostic error. As described above, according to the ultrasound diagnostic apparatus 1, it is possible to ensure safety for an object and the ultrasound diagnostic apparatus 1 and prevent diagnostic errors. In addition, since the probe identification information list is encrypted by a predetermined method, safety against information leakage is ensured.

Third Embodiment

The third embodiment differs from the first and second embodiments in that it is configured to determine consistency between the probe ID generated based on electrical states and probe identification information associated with a return signal.

Figure 7:
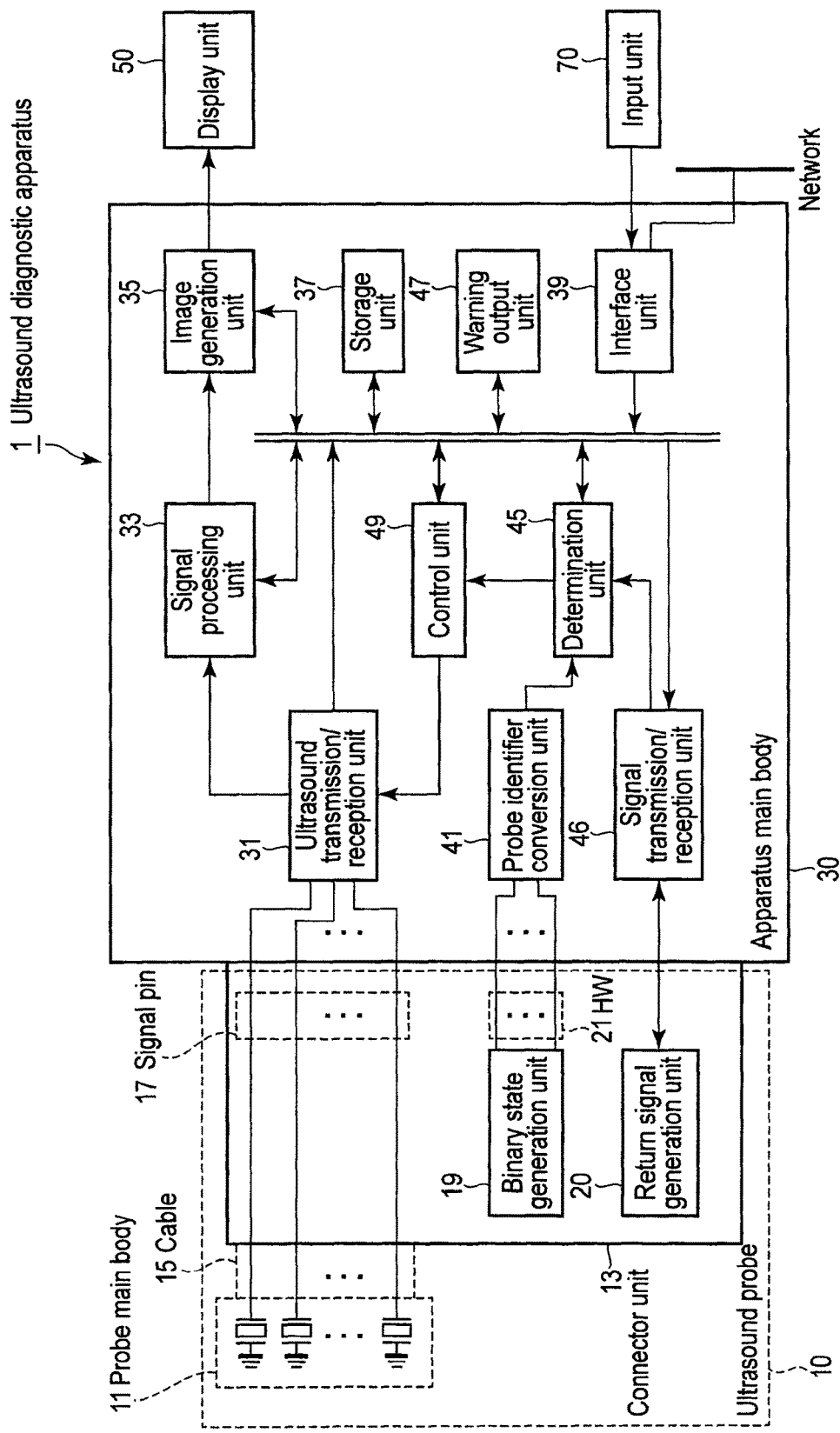
FIG. 7 is a block diagram showing an example of the arrangement of an ultrasound diagnostic apparatus according to the third embodiment.

FIG. 7 is a block diagram showing an example of the arrangement of an ultrasound diagnostic apparatus 1 according to the third embodiment. As shown in FIG. 7, a connector unit 13 further includes a return signal generation unit 20. An apparatus main body 30 further includes a signal transmission/reception unit 46.

When the connector unit 13 of an ultrasound probe 10 is connected to the apparatus main body 30, the signal transmission/reception unit 46 generates a predetermined transmission signal to be transmitted to the return signal generation unit 20 (to be described later). The signal transmission/reception unit 46 transmits the generated predetermined transmission signal. The signal transmission/reception unit 46 receives the return signal returned from the return signal generation unit 20. The signal transmission/reception unit 46 stores a correspondence table of probe identification information corresponding to return signals. The signal transmission/reception unit 46 generates probe identification information based on a return signal and the correspondence table. The signal transmission/reception unit 46 outputs the probe identification information to a determination unit 45.

Upon receiving a predetermined transmission signal, the return signal generation unit 20 generates a return signal. The return signal generation unit 20 outputs the generated return signal to the signal transmission/reception unit 46. Note that the return signal generation unit 20 may include a logic circuit (not shown) which generates a returns signal based on the input predetermined transmission signal.

The determination unit 45 determines consistency between the probe ID converted by a probe identifier conversion unit 41 and probe identification information. The determination unit 45 outputs the consistency determination result to a warning output unit 47 and a control unit 49 (both of which will be described later).

Note that the ultrasound diagnostic apparatus 1 according to the third embodiment may be provided with a memory 23, a memory connection pin 29, and a read unit 43 instead of a binary state generation unit 19, HWs 21, and the probe identifier conversion unit 41. In this case, the determination unit 45 determines consistency between the probe identification information read out from the memory 23 by the read unit 43 and the probe identification information output from the signal transmission/reception unit 46.

(Consistency Determination Function)

The consistency determination function is a function concerning a procedure for determining consistency between the probe ID generated based on electrical states and the probe identification information associated with a return signal. Processing concerning the consistency determination function (to be referred to as consistency determination processing hereinafter) will be described below.

FIG. 8 is a flowchart showing a procedure for consistency determination processing. The ultrasound probe 10 is connected to the apparatus main body 30 (step Sc1). The apparatus converts electrical states in the binary state generation unit 19 into a probe ID (step Sc2). The apparatus outputs the converted probe ID to the determination unit 45. The apparatus generates a predetermined transmission signal (step Sc3). The apparatus transmits the generated predetermined transmission signal to the return signal generation unit 20 (step Sc4). The apparatus generates probe identification information based on a return signal and the correspondence table (step Sc5). The apparatus outputs the generated probe identification information to the determination unit 45 (step Sc6). The determination unit 45 collates the probe identification information with the probe ID (step Sc7). If the probe identification information matches the probe ID (step Sc8), the apparatus controls an ultrasound transmission/reception unit 31 to execute ultrasound transmission/reception. If the probe identification information does not match the probe ID (step Sc8), the apparatus stops access to the ultrasound transmission/reception unit 31 (step Sc9). At this time, the apparatus outputs a predetermined warning to the warning output unit 47.

According to the above arrangement, the following effects can be obtained.

The ultrasound diagnostic apparatus 1 of this embodiment can determine consistency between the probe ID obtained by converting the electrical states stored in the binary state generation unit 19 provided in the ultrasound probe 10 and the probe identification information generated based on a return signal and a correspondence table. If the probe ID does not match the probe identification information, the apparatus can stop access to the ultrasound transmission/reception unit 31. In addition, the apparatus can output a predetermined warning such as an error message. Furthermore, the apparatus can display an error message or the like on the display unit 50.

As described above, even if an unguaranteed probe is erroneously connected to the apparatus main body 30 of the ultrasound diagnostic apparatus 1, it is possible to solve the problem of erroneous recognition of the unguaranteed probe. Even if an unguaranteed probe is erroneously connected to the apparatus main body 30, this makes it possible to avoid possibilities such as a malfunction in the ultrasound diagnostic apparatus 1 due to the inability to perform proper control and setting on the ultrasound probe, an injury on an object due to the generation of heat by the ultrasound probe, and an diagnostic error. As described above, according to the ultrasound diagnostic apparatus 1, it is possible to ensure safety for an object and the ultrasound diagnostic apparatus 1 and prevent diagnostic errors.

Fourth Embodiment

The fourth embodiment differs from the first to third embodiments in that it is configured to store the probe identification information encrypted based on probe use history information and the probe use history information, decrypt the probe identification information encrypted based on probe use history information in a memory 23, determine consistency between the probe ID generated based on electrical states and the decrypted probe identification information.

FIG. 9 is a block diagram showing an example of the arrangement of an ultrasound diagnostic apparatus 1 according to the fourth embodiment. As shown in FIG. 9, an apparatus main body 30 further includes an encryption write unit 32 and a readout decryption unit 34.

When probe use history information is updated, the encryption write unit 32 encrypts probe identification information based on the probe use history information. A control unit 49 updates the probe use history information in accordance with the end of the use of an ultrasound probe 10. The encryption write unit 32 writes the encrypted probe identification information and the probe use history information used for encryption in the memory 23.

Note that the encryption write unit 32 may be mounted on a connector unit 13. In this case, the encryption write unit 32 operates on an internal power supply (not shown) mounted on the connector unit 13 to encrypt probe identification information by using encryption information which has changed in time series and write the encrypted information in the memory 23. When the connector unit 13 is connected to the apparatus main body 30, the encryption write unit 32 outputs the time-series information used for the generation of encryption information which has changed in time series to the readout decryption unit 34.

When the connector unit 13 of the ultrasound probe 10 is connected to the apparatus main body 30, the readout decryption unit 34 reads out the encrypted probe identification information and the probe use history information from the memory 23. The readout decryption unit 34 decrypts the encrypted probe identification information by using the probe use history information. The readout decryption unit 34 outputs the decrypted probe identification information to a determination unit 45.

When the encryption write unit 32 is mounted on the connector unit 13, the readout decryption unit 34 decrypts encrypted probe identification information based on time-series information. The readout decryption unit 34 outputs the decrypted probe identification information to the determination unit 45.

The determination unit 45 determines consistency between the probe ID converted by a probe identifier conversion unit 41 and the decrypted probe identification information. The determination unit 45 outputs the consistency determination result to the warning output unit 47 and the control unit 49.

(Consistency Determination Function)

The consistency determination function is a function concerning a procedure for determining consistency between the probe ID converted by the probe identifier conversion unit 41 and decrypted probe identification information. Processing concerning the consistency determination function (to be referred to as consistency determination processing hereinafter) will be described below.

FIG. 10 is a flowchart showing a procedure for consistency determination processing. The ultrasound probe 10 is connected to the apparatus main body 30 (step Sd1). The apparatus converts electrical states in a binary state generation unit 19 into a probe ID (step Sd2). The apparatus outputs the converted probe ID to the determination unit 45. The apparatus reads out encrypted probe identification information and probe use history information from the memory 23 (step Sd3). The apparatus decrypts the readout probe identification information by using the probe use history information (step Sd4). The apparatus collates the decrypted probe identification information with the probe ID (step Sd5). If the probe identification information matches the probe ID (step Sd6), the apparatus controls the ultrasound transmission/reception unit 31 to execute ultrasound transmission/reception. After the use of the ultrasound probe 10, the apparatus updates the probe use history information. Upon updating of the probe use history information, the apparatus encrypts the probe identification information based on the probe use history information. The apparatus writes the encrypted probe identification information and the probe use history information used for encryption in the memory 23.

If the probe identification information does not match the probe ID (step Sd6), the apparatus stops access to the ultrasound transmission/reception unit 31 (step Sd7). At this time, a warning output unit 47 outputs a predetermined warning.

According to the above arrangement, the following effects can be obtained.

The ultrasound diagnostic apparatus 1 of this embodiment stores the probe identification information encrypted based on probe use history information and the probe use history information in the memory 23, and decrypts the probe identification information encrypted based on the probe use history information. The apparatus can determine consistency between the probe ID generated based on electrical states and the decrypted probe identification information. If the probe ID does not match the probe use history information, the apparatus can stop access to the ultrasound transmission/reception unit 31. In addition, the apparatus can output a predetermined warning such as an error message. Furthermore, the apparatus can display an error message or the like on a display unit 50.

If the probe identification information matches the probe ID, the ultrasound diagnostic apparatus 1 can update the probe use history information after the end of the use of the ultrasound probe 10, and encrypt the probe identification information based on the probe use history information. The ultrasound diagnostic apparatus 1 then can write the encrypted probe identification information and the probe use history information used for encryption in the memory 23.

As described above, even if an unguaranteed probe is erroneously connected to the apparatus main body 30 of the ultrasound diagnostic apparatus 1, it is possible to solve the problem of erroneous recognition of the unguaranteed probe. Even if an unguaranteed probe is erroneously connected to the apparatus main body 30, this makes it possible to avoid possibilities such as a malfunction in the ultrasound diagnostic apparatus 1 due to the inability to perform proper control and setting on the ultrasound probe, an injury on an object due to the generation of heat by the ultrasound probe, and an diagnostic error. In addition, since the probe identification information is encrypted by using probe use history information and stored in the memory 23, safety against information leakage can be ensured. As described above, according to the ultrasound diagnostic apparatus 1, it is possible to ensure safety for an object and the ultrasound diagnostic apparatus 1 and prevent diagnostic errors.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An ultrasound diagnostic apparatus, comprising:
an ultrasound probe including a plurality of transducers, a first memory, and binary state generation circuitry;
an apparatus main body to which the ultrasound probe is connected;
a second memory included in the apparatus main body and storing list information concerning a plurality of probe identifiers respectively corresponding to a plurality of ultrasound probes; and
processing circuitry included in the apparatus main body, wherein the first memory stores probe use history information and encrypted probe identification information, the encrypted probe identification information being encrypted based on the probe use history information by the processing circuitry; and
the binary state generation circuitry is configured to generate a binary electrical state; and
the processing circuitry is further configured to
convert the binary electrical state into a probe identifier;
read the encrypted probe identification information and the probe use history information from the first memory;
decrypt the encrypted probe identification information based on the probe use history information;
determine whether there is first consistency between the probe identifier and the stored list information;
determine whether there is second consistency between the decrypted probe identification information and the stored list information; and
output a predetermined warning when there is not at least one of the first consistency and the second consistency.

2. The apparatus of claim 1, further comprising:
ultrasound transmission and reception circuitry configured to transmit and receive ultrasound to and from an object via the transducers; and
control circuitry configured to control the ultrasound transmission and reception circuitry not to transmit or receive the ultrasound when the processing circuitry determines that there is not at least one of the first consistency and the second consistency.

3. The apparatus of claim 1, further comprising:
ultrasound transmission and reception circuitry configured to transmit and receive ultrasound to and from an object via the transducers; and
control circuitry configured to disable access to the ultrasound transmission and reception circuitry when the processing circuitry determines the that there is not at least one of the first consistency and the second consistency.

4. The apparatus of claim 1, wherein the processing circuitry is further configured to, when a use of the ultrasound probe ends, update, in the first memory of the ultrasound probe, the probe use history information, encrypt the decrypted probe identification information based on the updated probe use history information, and write the newly encrypted probe identification information into the first memory to be stored together with the updated probe use history information.

* * * * *